(12) United States Patent
Kim

(10) Patent No.: US 10,470,282 B2
(45) Date of Patent: Nov. 5, 2019

(54) STATIC ELECTRICITY REMOVAL BOOTH

(71) Applicant: ESGK CO., LTD., Daejeon (KR)

(72) Inventor: Kwi Young Kim, Daejeon (KR)

(73) Assignee: ESGK CO., LTD., Daejeon (KR)

( * ) Notice: Subject to any disclaimer, the term of this patent is extended or adjusted under 35 U.S.C. 154(b) by 219 days.

(21) Appl. No.: 15/553,123

(22) PCT Filed: Oct. 29, 2015

(86) PCT No.: PCT/KR2015/011506
§ 371 (c)(1),
(2) Date: Aug. 23, 2017

(87) PCT Pub. No.: WO2016/137086
PCT Pub. Date: Sep. 1, 2016

(65) Prior Publication Data
US 2018/0054878 A1    Feb. 22, 2018

(30) Foreign Application Priority Data
Feb. 25, 2015  (KR) .................. 10-2015-0026500

(51) Int. Cl.
*H05F 3/00*  (2006.01)
*H05F 3/02*  (2006.01)
(Continued)

(52) U.S. Cl.
CPC ............... *H05F 3/00* (2013.01); *A61N 1/16* (2013.01); *B05B 1/02* (2013.01); *B05B 11/30* (2013.01);
(Continued)

(58) Field of Classification Search
USPC ......................................... 361/216
See application file for complete search history.

(56) References Cited

U.S. PATENT DOCUMENTS 4,169,279 A * 9/1979 Friedman, Jr. ............ H05F 3/00
361/212
6,387,081 B1 * 5/2002 Cooper .................. A61M 35/00
604/289
(Continued)

FOREIGN PATENT DOCUMENTS

JP    H06-349591 A   12/1994
JP    2921762 B2    7/1999
(Continued)

*Primary Examiner* — Ronald W Leja
(74) *Attorney, Agent, or Firm* — Korus Patent, LLC; Seong Il Jeong

(57) ABSTRACT

The present invention relates to a static electricity removal booth, and more specifically to a static electricity removal booth which measures and displays the amount of static electricity accumulated in a human body before entrance into or exit from an explosion-proof area where an inflammable, such as gunpowder, refined petroleum or inflammable gas, is handled, allows an enterer to enter the inside of the static electricity removal booth when a voltage equal to or higher than an allowable value is measured, removes the bodily static electricity by bringing sprayed moisture including a conductive material into contact with the enterer in an omnidirectional manner, and then allows the enterer to enter the explosion-proof area, thereby preventing an explosion accident attributable to human body-accumulated static electricity from occurring.

6 Claims, 4 Drawing Sheets

(51) Int. Cl.
    *B05B 15/65*     (2018.01)
    *B05B 1/02*     (2006.01)
    *B05B 11/00*     (2006.01)
    *B05B 12/00*     (2018.01)
    *A61N 1/16*     (2006.01)
    *B05B 16/00*     (2018.01)

(52) U.S. Cl.
    CPC ............ *B05B 12/002* (2013.01); *B05B 15/65* (2018.02); *B05B 16/00* (2018.02); *H05F 3/02* (2013.01)

(56) References Cited

U.S. PATENT DOCUMENTS

2017/0350066 A1\*   12/2017   Kim ..................... D06F 58/203
2018/0054878 A1\*   2/2018   Kim ......................... H05F 3/00

FOREIGN PATENT DOCUMENTS

| | | |
|---|---|---|
| JP | 2015-011957 A | 1/2015 |
| KR | 20-0151780 Y1 | 7/1999 |
| KR | 20-0392190 Y1 | 8/2005 |
| KR | 10-1167964 B1 | 7/2012 |
| KR | 10-1333635 B1 | 11/2013 |

\* cited by examiner

STATIC ELECTRICITY REMOVAL BOOTH

TECHNICAL FIELD

The present invention relates to a static electricity removal booth, and more specifically to a static electricity removal booth which measures and displays the amount of static electricity accumulated in a human body before entrance into or exit from an explosion-proof area where an inflammable, such as gunpowder, refined petroleum or inflammable gas, is handled, allows an enterer to enter the inside of the static electricity removal booth when a voltage equal to or higher than an allowable value is measured, removes the bodily static electricity by bringing sprayed moisture including a conductive material into contact with the enterer in an omnidirectional manner, and then allows the enterer to enter the explosion-proof area, thereby preventing an explosion accident attributable to human body-accumulated static electricity from occurring.

BACKGROUND ART

Generally, high and low currents flow through a product using electricity, and thus the electric product is operated, in which case static electricity is generated in a charged object by electric charges. Unlike the movement of current generated by the general flow of charges, static electricity is characterized in that static electricity remains on the surface of a charged object without the flow of charges, maintains a predetermined voltage, and is discharged to thus generate discharge current at the moment of the removal of electricity.

When electrostatic discharge occurs, electrostatic energy maintained by charges is released to a discharge space. An unexpected problem may occur due to a spark which may be generated during a discharge process. For example, the problem includes the ignition and explosion of inflammable gas, an electrical impact on a human body, a damage to a living body such as a damage to a skin, the destruction of a semiconductor device, poor painting and printing, the exposure of a photo film, the erroneous operation of an electronic device attributable to electronic noise, etc.

In particular, a large amount of oil mist may be generated or inflammable gas may leak in areas where inflammables are handled, such as an area where petroleum is refined, such as a petrochemical factor or an oil refinery, an area where gunpowder or the like is handled, an area where inflammable gas is handled, etc. Accordingly, there is a risk that fire explosion occurs due to a spark which may be generated in a process of discharging static electricity under high voltage.

Accordingly, such areas are designated as explosion-proof areas where fire explosion is prevented from occurring, from which all risky factors which may act as ignition sources are removed. In each facility, grounding is performed via a plurality of static electricity removal apparatuses, and static electricity is discharged to the surface of the earth, thereby preventing a fire explosion accident attributable to the accumulation of static electricity from occurring.

In such an explosion-proof area, static electricity accumulated in the body of an enterer may act as an ignition source for fire explosion. Accordingly, human body-accumulated static electricity is removed by applying a static electricity removal apparatus not only to a facility but also to an enterer.

Conventionally, human body-accumulated static electricity has been removed using various methods. For example, a task is performed with a ground line connected to clothes, or static electricity is discharged through passage through a conductive mat.

However, according to the method, an enterer cannot be notified of the amount of human body-accumulated static electricity, and does not become aware of the importance of a process of removing static electricity. Accordingly, the enterer enters an explosion-proof area in the state in which the enterer has not appropriately performed a process of removing static electricity, and thus there is the risk of fire explosion.

Korean Utility Model Registration No. 20-0151780 (registered on Apr. 20, 1999; hereinafter referred to as "prior art document 1") presents a static electricity removal apparatus. Prior art document 1 presents a static electricity removal apparatus, the static electricity removal apparatus being provided in a clean room and removing static electricity attributable to a human body, which is generated in the clothes of an operator and is a cause of the destruction of a semiconductor device, the static electricity removal apparatus comprising: at least one air spray means provided at a predetermined location on the surface of the inner wall of the clean room, and configured to spray clean air, supplied from the outside, for a predetermined period in order to separate particles remaining on clothes; at least one vapor spray means provided at a predetermined location on one side of the air spray means, and configured to spray vapor to the clothes for a predetermined period in order to discharge static electricity attributable to a human body into the air; a duct provided at a predetermined location on the surface of the wall of the clean room, configured to remove the particles separate from clothes and dry moisture through suction, and made of a conductive material so that all charged objects, including the static electricity discharged into the air, within the clean room can flow; and a ground mat connected to the duct, and configured to ground the charged objects flowing along the duct. The static electricity removal apparatus of prior art document 1 is a static electricity removal means used in the field of the manufacture of semiconductors, and is configured such that a moisture spray opening is installed in the inner wall of the building of a clean room designed to fundamentally block the inflow of impurities and static electricity is discharged by spraying moisture.

The static electricity removal apparatus of prior art document 1 is similar to the present invention in which static electricity is discharged into the air by spraying vapor in order to prevent semiconductor productivity from being reduced due to impurities and charged objects. However, the static electricity removal apparatus of prior art document 1 is inconvenient in that an enterer has to rotate in order to spray vapor to the overall body of the enterer during a process of spraying vapor because openings configured to spray vapor are formed in both side walls to face each other, is disadvantageous in that the static electricity removal apparatus is integrated with a building at an entrance to the building in which a semiconductor production line is installed and thus has poor mobility, and is problematic in that it is difficult for a user to become aware of a risk regarding static electricity because information about human body-accumulated static electricity is not provided.

Korean Patent No. 10-1167964 (registered on Jul. 17, 2012; hereinafter referred to as "prior art document 2") presents a static electricity detection and removal apparatus. The static electricity detection and removal apparatus of prior art document 2 was filed and patented by the present inventor, comprises: a static electricity detection unit configured to come into contact with an object, a body configured to include a display module and a bypass module, a lower support part configured to include a ground module and a power module, and a connection part configured to connect the body with the lower support part, and to connect static electricity and power via different lines, and displays the amount of static electricity accumulated while removing static electricity by using a method in which an object makes a direct contact. Although the static electricity detection and removal apparatus of prior art document 2 has the effect of reducing static electricity to a dangerous level or lower by using the contact method, there is some difficulty in removing static electricity accumulated in clothes because a contact portion is limited.

Therefore, there is a need for research into a static electricity removal apparatus having a new structure, which can increase efficiency in removing static electricity accumulated in clothes by increasing a contact area through the application of a static electricity removal method based on the spray of moisture and can remove static electricity by spraying moisture to the front side of an enterer without requiring a user to rotate.

DISCLOSURE

Technical Problem

An object of the present invention is to provide a static electricity removal booth which is installed at an entrance to an explosion-proof area, measures and displays the amount of human body-accumulated static electricity of an enterer during entrance or exit, and sprays vapor including a conductive material in an inner spray chamber when a predetermined or larger amount of static electricity is measured, thereby removing human body-accumulated static electricity by discharging the human body-accumulated static electricity.

Furthermore, an object of the present invention is to provide an apparatus in which a spray chamber has a structure in which moisture sprayed from a front side is sprayed to the back side of an enterer without rotation during a process of spraying moisture to the enterer by means of the inner wall surface of the spray chamber and the spray directions of moisture spray holes, thereby conveniently removing static electricity.

Technical Solution

In order to solve the above technical problems, the present invention provides a static electricity removal booth, the static electricity removal booth being installed at an entrance to an explosion-proof area and measuring and removing human body-accumulated static electricity, the static electricity removal booth including: a body configured such that a spray chamber, which is a space portion, is formed therein, the body is a container body closed except for an entrance connecting the spray chamber with the outside, and the bottom surface of the spray chamber is grounded to the surface of the earth; a plurality of moisture spray holes disposed in the inner wall of the spray chamber of the body, and configured to spray moisture in a fog form; a pump installed inside the body, and configured to transfer moisture, contained in the body or supplied from the outside, to the moisture spray holes under high pressure; a control panel installed on the outer surface of the body and on the inside of the body, and configured to discharge human body-accumulated static electricity in response to the contact of an enterer, to display the amount of static electricity during a discharging process, and to include a control unit configured to control the flows of various types of signals.

The spray chamber of the body may be configured such that the front and both side surfaces of the inner are formed to be a circular or elliptical curved surface, and the back sides of the inner wall, which are both sides of the entrance, are formed to be recessed surfaces which are recessed toward the center of the spray chamber to have a hook-shaped section; and the moisture spray holes may be vertically formed in the front surface of the inner wall of the spray chamber in a plurality of rows, and may be configured such that moisture sprayed to both side surfaces of the inner wall moves along the surface of the inner wall, swerves on the recessed surface, and collides with the back side of the enterer.

The moisture spray holes arranged in the plurality of rows may spray moisture so that moisture spray holes arranged in one side column spray moisture to a side surface of the inner wall adjacent to moisture spray holes arranged in the other side column and sprayed moistures cross each other.

The control panel may include: a touchpad installed on the outer surface of one side of the entrance on the front surface of the body, and configured to include an electric discharge module configured to receive static electricity from the enterer and to discharge the static electricity through grounding; a display unit located on a portion of the front surface of the body above the entrance or touchpad, and configured to display a value corresponding to the amount of static electricity during a discharge process; a sound output unit configured to output a warning sound when the value displayed on the display unit is equal to or higher than a set value; and a control unit configured to control signals regarding the display of the static electricity and the output of the sound and to control the flows of signals including an operating signal of the pump.

Advantageous Effects

The static electricity removal booth of the present invention according to the technical solution measures and displays static electricity accumulated in a human body before entrance into or exit from an explosion-proof area where oil mist is generated or an inflammable is handled, allows an enterer to enter a spray chamber when a predetermined or larger amount of static electricity is measured, and removes the human body-accumulated static electricity by spraying moisture including a transition metal component in a vapor form, thereby preventing an explosive fire attributable to human body-accumulated static electricity within the explosion-proof area.

Furthermore, there can be provided a useful apparatus in which moisture can be sprayed to all the sides of an entered enterer by using the moisture spray holes formed only in one side surface in such a manner that moisture sprayed from the front surface of the spray chamber to both sides swerves along the surface of the inner wall including the curved surfaces and the recessed surfaces and collides with the back surface of the enterer, etc., and thus the number of moisture spray holes is reduced and the capacity of the pump configured to provide moisture spray pressure is also reduced, thereby reducing a manufacturing cost.

DESCRIPTION OF REFERENCE SYMBOLS OF PRINCIPAL COMPONENTS IN THE DRAWINGS

Figure 1:
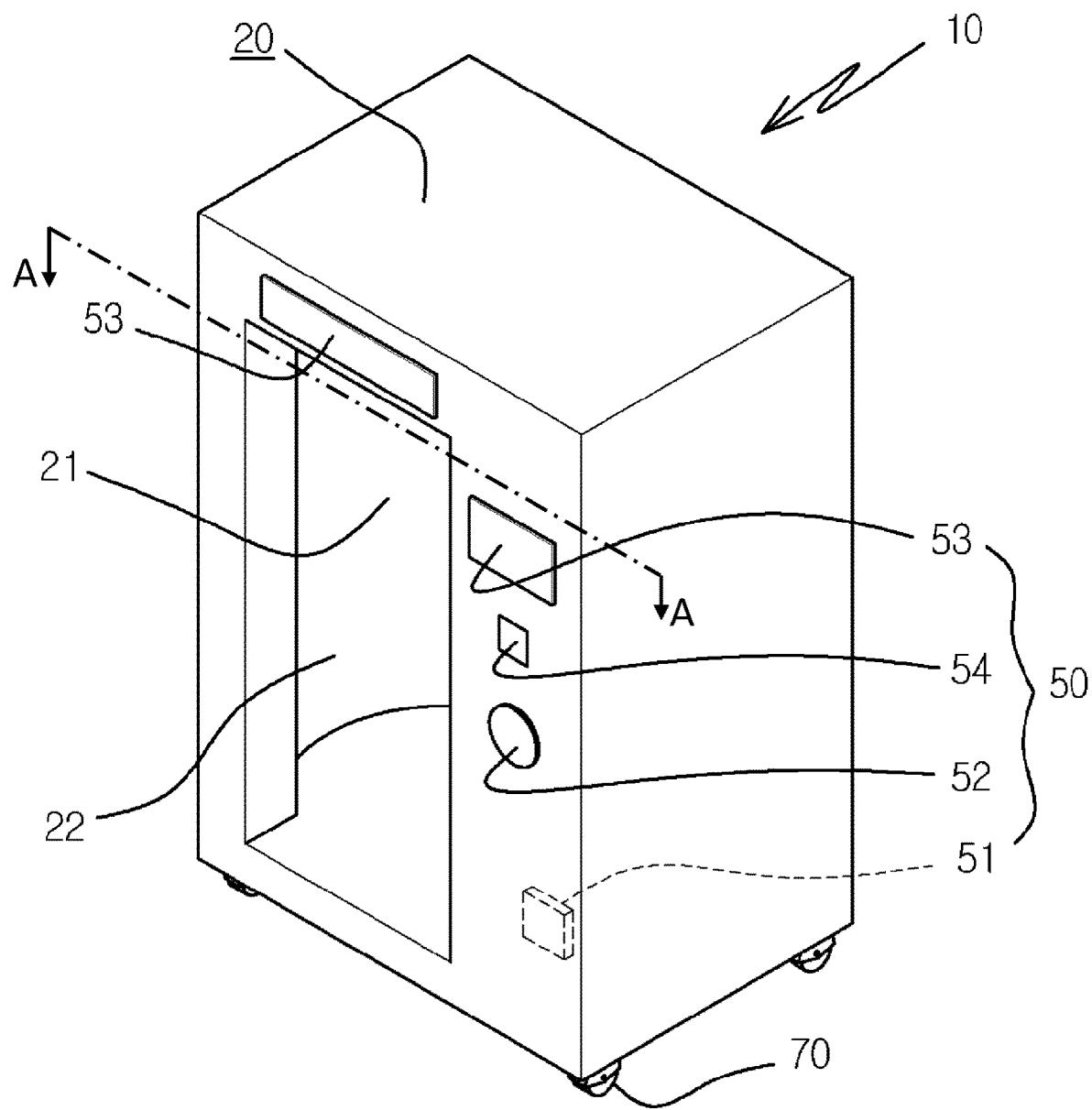
FIG. 1 is a schematic perspective view of a static electricity removal booth according to a preferred embodiment of the present invention.

10: static electricity removal booth
20: body
21: spray chamber
22: entrance
211: recessed surface
30: moisture spray hole
40: pump
50: control panel
51: control unit
52: touchpad
53: display unit
54: sound output unit
55: power supply unit
60: moisture storage tank
70: caster

BEST MODE

The present invention may be subjected to various modifications, and may have various embodiments. Specific embodiments will be illustrated in the accompanying drawings, and will be described in the following detailed description. However, this is not intended to limit the present invention to the specific embodiments. It should be understood that the present invention includes all modifications, equivalents and replacements included in the spirit and technical range of the present invention.

Figure 2:
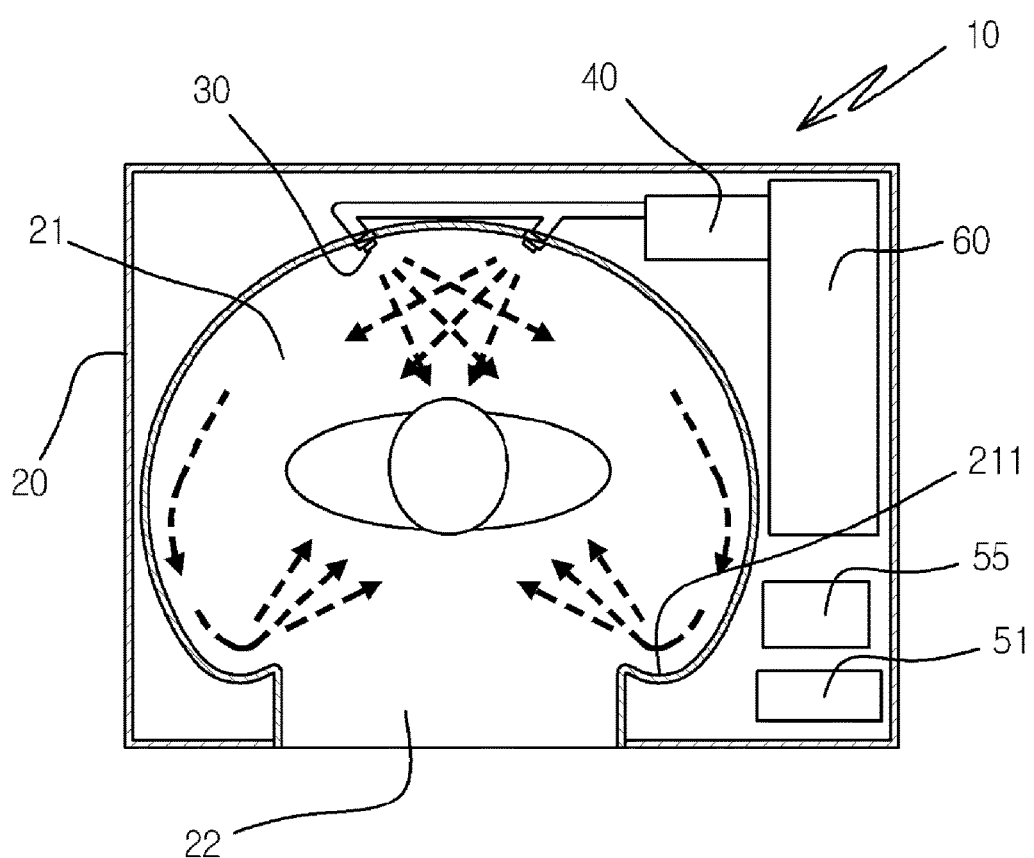
FIG. 2 is a sectional view schematically showing the horizontal section of portion A-A of FIG. 1.

FIG. 1 is a schematic perspective view of a static electricity removal booth according to a preferred embodiment of the present invention, and FIG. 2 is a sectional view of portion A-A of FIG. 1.

As shown in the drawings, a static electricity removal booth 10 according to the present invention is configured to include: a body 20 configured such that a spray chamber 21, which is a space portion, is formed therein; a plurality of moisture spray holes 30 disposed in the spray chamber of the body; a pump 40 configured to supply high-pressure moisture to the moisture spray holes; and a control panel 50 formed on one side of the body.

The body 20 is a container body configured such that an entrance 22 is formed in the front surface thereof and the other surfaces thereof are closed, and may be fabricated into a booth having any one of various shapes including a polygonal section pillar and a circular section pillar in addition to the shown rectangular section shape.

The spray chamber 21, which is a space portion which an enterer can enter, is formed inside the body.

The spray chamber may be formed into a general rectangular or polygonal section space. As shown in FIG. 2, the inner wall of the spray chamber may be formed to be a curved surface.

The spray chamber 21 may be configured such that the front and both side surfaces of the inner wall in which the moisture spray holes 30 are disposed are formed to be a circular or elliptical curved surface and the back surfaces of the inner wall of the spray chamber, which are both sides of the entrance 22, are formed to be recessed surfaces 211 recessed toward the center of the spray chamber to have a hook-shaped form by making the curved angle of the back surfaces larger than that of the curved surface formed by the front and both side surfaces of the inner wall. In other words, the front surface of the inner wall of the spray chamber 21 of the present invention except for the entrance is formed to be a curved surface, and the recessed surfaces 211 are formed to face the center of the spray chamber by further increasing the curved angle of the surface of the inner wall on both sides of the entrance. This allows moisture, sprayed from the moisture spray holes 30 in a fog form, to come into contact with the surface of the inner wall of the spray chamber in an inclined manner, other than a vertical manner, at a predetermined angle, for example, ranging from 20 to 60°, thereby minimizing friction attributable to contact and thus allowing the currents of the sprayed moisture to move to the back side of an enterer. Furthermore, the sprayed moisture swerves on the recessed surfaces, and thus moisture sprayed via the moisture spray holes disposed in the front side is sprayed to the back side of the entered enterer.

Furthermore, the bottom surface of the spray chamber 21 is made of a conductive material, and is grounded to the surface of the earth, thereby enabling electric discharge to be performed when an enterer enters.

Next, the plurality of moisture spray holes 30, 30a and 30b is formed in the front portion of the inner wall of the spray chamber. A plurality of moisture spray holes 30a may be formed in a plurality of columns and a plurality of rows and performs spray, as shown in FIG. 3a, or a plurality of moisture spray holes 30b may be formed in a single column and in a plurality of rows, as shown in FIG. 3b.

Figure 3A:
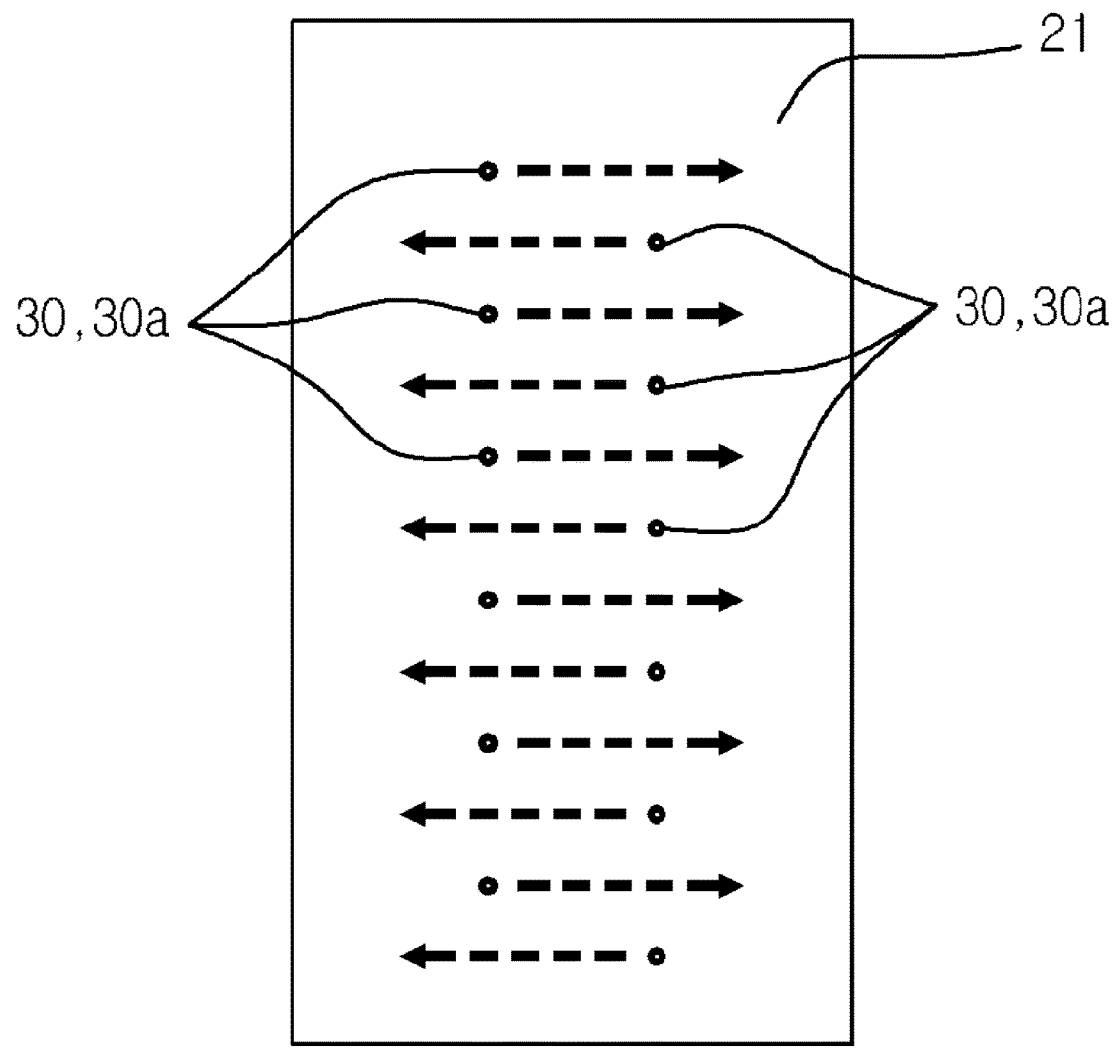
FIGS. 3a and 3b are schematic diagrams showing examples of the installation of moisture spray holes according to the present invention.

In the case of the moisture spray holes 30a arranged in the plurality of columns, as shown in FIG. 3a, the spray direction of the moisture spray holes arranged along one column and the spray direction of the moisture spray holes arranged along the other column may be made different, and thus moisture may be sprayed to both sides of an enterer which has entered the spray chamber. In this case, the moisture spray holes 30a arranged in the plurality of columns may be configured to spray moisture in crossing directions, thereby enabling moisture to be sprayed to the front side of an enterer while reducing a spray or contact angle with respect to the inner wall surface of the spray chamber. Furthermore, in order to prevent the spray currents of the sprayed moisture from intersecting each other and thus slowing down during a cross spray process, the moisture spray holes arranged along one column and the moisture spray holes arranged along the other column are arranged at different heights in a zigzag manner, as shown in the drawing, thereby preventing the currents of moisture, sprayed from the moisture spray holes 30a, from being obstructed.

Figure 3B:
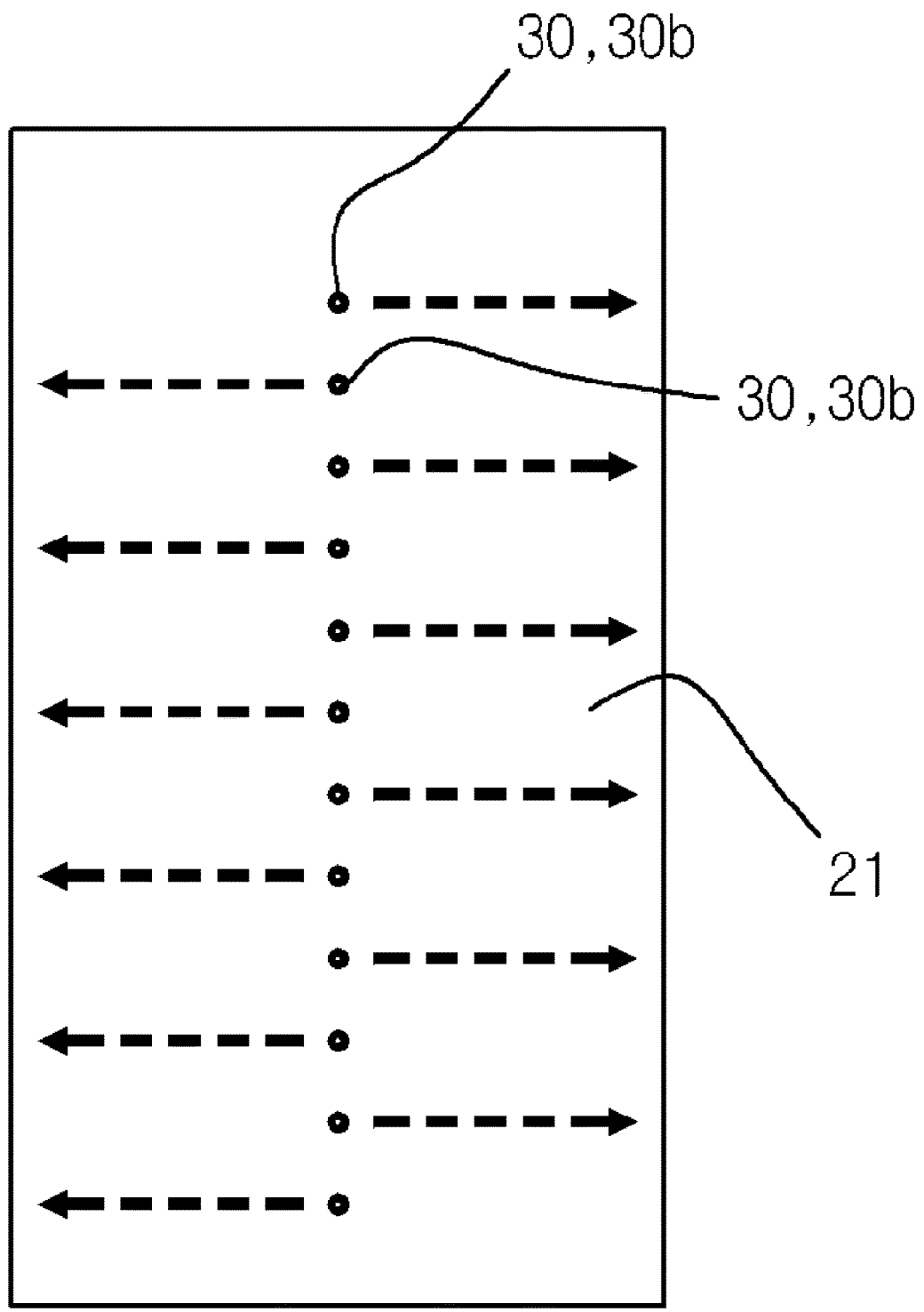

Furthermore, in the case where the moisture spray holes 30b are arranged in a single column, as shown in FIG. 3b, the plurality of moisture spray holes 30b arranged in a vertical direction are configured to spray moisture in a lateral zigzag manner, thereby enabling moisture to be sprayed to both sides.

Furthermore, the pump 40 is installed inside the body, and is disposed in a space between the spray chamber 21 and the outer surface of the body. The pump 40 receives moisture from the outside or receives stored moisture, and supplies moisture to the individual moisture spray holes 30 via supply lines under high pressure, thereby enabling moisture to be sprayed via the moisture spray holes in a fog form. The pump 40 may be operated through the manipulation of a switch installed on the outer surface of the body or in the spray chamber, or may be automatically operated for a predetermined period by installing a sensor in the spray chamber and detecting the entrance of an enterer when the enterer enters the spray chamber.

The body 20 may be pipe-connected to a moisture supply source in the outside, and moisture may be directly supplied from the moisture supply source and provided by the pump. Alternatively, as shown in the drawing, a moisture storage tank 60 may be further provided in the space between the spray chamber and the outer surface of the body, may store a predetermined amount of moisture, and may supply the stored moisture to the moisture spray holes.

The moisture storage tank 60 may be equipped with a commonly used moisture level detection device based on buoyancy or a sensor, may receive and store moisture when a moisture level falls to a level equal to or lower than a predetermined moisture level. With regard to a method of supplying moisture, a user may supply moisture, or a water service line may be connected and then moisture may be supplied.

Furthermore, a conductive material supply device may be installed on one side of the moisture storage tank 60, and a conductive material may be automatically introduced in response to the manipulation of a button or the supply of moisture to the moisture storage tank, thereby enabling electric discharge attributable to the supply of moisture to be performed. The conductive material may typically include transition metals and compounds including transition metals, may further include various conductive materials.

Furthermore, the body 20 may include drainage or exhaust equipment configured to discharge moisture sprayed in the spray chamber. For example, drainage equipment may be formed in the bottom surface, may collect sprayed moisture, and may then discharge the moisture to the outside. Alternatively, an exhaust fan may be constructed in the upper space of the spray chamber moisture, and may discharge moisture sprayed in a fog form.

Furthermore, casters 70 may be installed on the bottom of the body 20, and may thus facilitate the movement of the body 20. In this case, the casters may be configured to be selectively lifted and lowered by hydraulic pressure, and may be lowered and used only when required. Alternatively, a fastening rod may be further provided, and the installation locations of the casters 70 may be fastened by the fastening rod.

Next, the control panel 50 is a configuration including a touchpad 52 located on one side of the surface in which the entrance is formed, i.e., the front surface of the body, a display unit 53, a sound output unit 54, and a control unit 51 configured to control various types of internal signals and the power of the power supply unit 55.

The touchpad 52 is exposed through one side of the front surface of the body 20 in which the entrance 22 is formed, and is a component with which an enterer who enters or exits an explosion-proof area brings his or her hand or part of a human body into contact. The touchpad 52 is provided with an electric discharge module, and removes human body-accumulated static electricity received from an enterer by flowing the static electricity to the surface of the earth via a ground.

The display unit 53 is a component which is installed at any one or both of a portion of the front surface of the body above the entrance 22 and a portion of the front surface of the body above the touchpad and provides information about the amount of static electricity. In other words, during a process in which human body-accumulated static electricity is grounded by means of the electric discharge module, the human body-accumulated static electricity is converted into a value corresponding to the flowing static electricity by a control module and generated as a corresponding signal, and the generated corresponding signal is transmitted to the display unit 53 and displayed to the outside. In other words, the level of the voltage of the human body-accumulated static electricity is measured and displayed, and thus an enterer is notified of human body-accumulated static electricity, thereby enabling the enterer to operate and repair facilities while considering the risk of the static electricity. Furthermore, the control module generally includes a device or circuit configured to measure voltage.

The sound output unit 54 outputs a warning sound adapted to issue a warning when the voltage of static electricity transmitted to and displayed on the display unit 53 is detected as a value equal to or higher than a set value, thereby prompting a user to perform an additional static electricity removal process. For example, when the set voltage value is set to 1000 V, a measured static electricity voltage is measured as a value equal to or higher than 1000 V, the detected voltage is displayed on the display unit, and a warning sound indicative of a risk is output by the sound output unit.

Furthermore, when the voltage of static electricity is detected as a value equal to or higher than the set value, not only the warning sound of the sound output unit but also the light emission of a lamp may be provided.

The control unit 51 controls various types of signals, such as signals regarding the measurement of the voltage of static electricity, the operation of the pump, etc., and blocks or allows the power supply of the power supply unit 55. In particular, the control includes the display of a measured voltage, the output of a warning sound output, and the operation of the pump and the control of operating time based on the sensor installed in the spray chamber or the operating signal of the moisture spray holes.

The operating state of the static electricity removal booth of the present invention will be described in brief below.

When an enterer who enters or exits an explosion-proof area comes into contact with the touchpad 52 of the static electricity removal booth 10 of the present invention, part of the human body-accumulated static electricity of the enterer is removed by being grounded via the touchpad.

In this case, the static electricity flowing into the surface of the earth and removed is generated as a signal corresponding to the voltage of the static electricity by the control module, the generated corresponding signal is transmitted to the display unit 53, and the level of the voltage of the static electricity is displayed to the outside.

When the measured voltage is detected as a value equal to or higher than a set value, a warning sound is output by the sound output unit 54, thereby allowing the enterer to enter the inner spray chamber 21.

When the enterer enters the spray chamber via the entrance 22 of the body, the internal sensor detects the entrance of the enterer and transmits a detection signal to the control unit, and the control unit transfers the moisture of the moisture storage tank 60 to the moisture spray holes 30 under high pressure by immediately operating the pump 40, thereby enabling moisture to be sprayed in a fog form via the moisture spray holes.

The moisture spray holes 30 enable moisture to remove static electricity accumulated in the outside of the clothes of an enterer by discharging the static electricity into the air while passing the moisture through the front side of the enterer in an inclined manner, and provide moisture so that moisture having collided with the inner wall of the spray chamber 21 due to spray pressure moves forward in the direction of the entrance along the curved surface of the inner wall of the spray chamber, swerves on the recessed surfaces 211, and collides with the back surface of an enterer standing at the center of the spray chamber, thereby enabling static electricity on the back portion (back side) of the enterer to be also removed.

As described above, the static electricity removal booth of the present invention enables static electricity to be removed by providing sprayed moisture not only to the front side of an enterer who has entered the spray chamber but also to the back side of the enterer via the moisture spray holes 30 disposed on the front side. Accordingly, the static electricity removal booth enables static electricity to be primarily removed by means of the touchpad and static electricity in clothes and also enables the remaining static electricity to be secondarily removed by means of moisture, and thus static electricity remaining in the enterer is maximally removed, thereby achieving the stable management of facilities.

The invention claimed is:

1. A static electricity removal booth, the static electricity removal booth being installed at an entrance to an explosion-proof area and measuring and removing human body-accumulated static electricity, the static electricity removal booth comprising:
   a body configured such that a spray chamber, which is a space portion, is formed therein, the body is a container body closed except for an entrance connecting the spray chamber with an outside, and a bottom surface of the spray chamber is grounded to a surface of an earth;
   a plurality of moisture spray holes disposed in an inner wall of the spray chamber of the body, and configured to spray moisture in a fog form;
   a pump installed inside the body, and configured to transfer moisture, contained in the body or supplied from the outside, to the moisture spray holes under high pressure;
   a control panel installed on an outer surface of the body and on an inside of the body, and configured to discharge human body-accumulated static electricity in response to contact of an enterer, to display an amount of static electricity during a discharging process, and to include a control unit configured to control flows of various types of signals.

2. The static electricity removal booth of claim 1, wherein:
   the spray chamber of the body is configured such that front and both side surfaces of the inner wall are formed to be a circular or elliptical curved surface, and back sides of the inner wall, which are both sides of the entrance, are formed to be recessed surfaces which are recessed toward a center of the spray chamber to have a hook-shaped section; and
   the moisture spray holes are vertically formed in the front surface of the inner wall of the spray chamber in a plurality of rows, and are configured such that moisture sprayed to both side surfaces of the inner wall moves along the surface of the inner wall, swerves on the recessed surface, and collides with a back side of the enterer.

3. The static electricity removal booth of claim 2, wherein the moisture spray holes arranged in the plurality of rows sprays moisture so that moisture spray holes arranged in one column spray moisture to a side surface of the inner wall adjacent to moisture spray holes arranged in a remaining column and currents of the sprayed moisture cross each other.

4. The static electricity removal booth of claim 1, wherein the control panel comprises:
   a touchpad installed on an outer surface of one side of the entrance on the front surface of the body, and configured to include an electric discharge module configured to receive static electricity from the enterer and to discharge the static electricity through grounding;
   a display unit located on a portion of the front surface of the body above the entrance or touchpad, and configured to display a value corresponding to the amount of static electricity during a discharge process;
   a sound output unit configured to output a warning sound when the value displayed on the display unit is equal to or higher than a set value; and
   the control unit configured to control signals regarding the display of the static electricity and the output of the sound and to control flows of signals including an operating signal of the pump.

5. The static electricity removal booth of claim 1, further comprising a moisture storage tank in a space between the spray chamber and an outer surface of the body in the body so that moisture is supplied to the moisture spray holes by the pump.

6. The static electricity removal booth of claim 1, further comprising casters on a bottom surface of the body.

* * * * *